(12) United States Patent
Paufique

(10) Patent No.: US 9,044,490 B2
(45) Date of Patent: Jun. 2, 2015

(54) **ACTIVE INGREDIENT OBTAINED FROM *CICHORIUM INTYBUS* FOR ACTING ON THE BARRIER FUNCTION OF THE SKIN THAT IS SIMILAR TO THAT OF VITAMIN D**

(71) Applicant: SOCIETE INDUSTRIELLE LIMOUSINE D'APPLICATION BIOLOGIQUE, Objat (FR)

(72) Inventor: Jean Paufique, Objat (FR)

(73) Assignee: SOCIETE INDUSTRIELLE LIMOUSINE D'APPLICATION BIOLOGIQUE, Objat (FR)

( * ) Notice: Subject to any disclaimer, the term of this patent is extended or adjusted under 35 U.S.C. 154(b) by 0 days.

(21) Appl. No.: 13/795,053

(22) Filed: Mar. 12, 2013

(65) Prior Publication Data
US 2013/0237496 A1 Sep. 12, 2013

(30) Foreign Application Priority Data
Mar. 12, 2012 (FR) ...................................... 12 52183

(51) Int. Cl.
| *A01N 43/04* | (2006.01) |
| *A61K 31/715* | (2006.01) |
| *A61K 31/702* | (2006.01) |
| *A61K 31/733* | (2006.01) |
| *A61Q 19/08* | (2006.01) |
| *A61K 8/97* | (2006.01) |
| *A61K 8/64* | (2006.01) |
| *A61K 36/28* | (2006.01) |

(52) U.S. Cl.
CPC ............. *A61K 31/702* (2013.01); *A61K 31/733* (2013.01); *A61Q 19/08* (2013.01); *A61K 8/97* (2013.01); *A61K 8/645* (2013.01); *A61K 36/28* (2013.01)

(58) Field of Classification Search
None
See application file for complete search history.

(56) References Cited

FOREIGN PATENT DOCUMENTS

| EP | 0326491 A1 | 8/1989 |
| JP | 63309147 A | 12/1988 |
| WO | 2005053710 A2 | 6/2005 |

OTHER PUBLICATIONS

Gennaro et al. Food Chemistry (2000), vol. 68, pp. 179-183.*
Vergauwen et al. Plant Physiol. (2003), vol. 133, pp. 391-401.*
Jurlique: "Night Cream"—Jurlique Herbal Recovery, Mintel, Feb. 1, 2011, XP055049025.
French Search Report, dated Jan. 22, 2013, from corresponding FR application.

* cited by examiner

*Primary Examiner* — Patrick Lewis
(74) *Attorney, Agent, or Firm* — Young & Thompson

(57) ABSTRACT

A *Cichorium intybus* root hydrolyzate including oligofructosans and its use as active ingredient designed for use in a composition with cutaneous application, for acting as a substitute for vitamin D on skin cells, and for making it possible to preserve and/or to repair the cutaneous barrier function. Also cosmetic compositions including this active ingredient and to a cosmetic skin-care process.

9 Claims, 4 Drawing Sheets

ACTIVE INGREDIENT OBTAINED FROM *CICHORIUM INTYBUS* FOR ACTING ON THE BARRIER FUNCTION OF THE SKIN THAT IS SIMILAR TO THAT OF VITAMIN D

FIELD OF THE INVENTION

This invention relates to a particular active ingredient that is obtained from the *Cichorium intybus* root and its use on skin in a composition with a topical application, for an action that is similar to that of vitamin D.

The invention also relates to the cosmetic compositions that include such molecules, and a process for cosmetic treatment that is designed to preserve or to accelerate the recovery of the barrier function of the skin.

BACKGROUND OF THE INVENTION

Vitamin D is well known for its essential role in monitoring phospho-calcium homeostasis and in bone mineralization. The synthesis of vitamin D is initiated at the level of the skin under the action of UVB rays and their biologically active form; calcitriol is then produced in the kidney to exert its functions.

Nevertheless, recently, it is known that there is also an autonomous cutaneous system for the production of calcitriol at the level of the skin, and the discovery of this system made it possible to reveal the involvement of vitamin D in other cutaneous cellular functions: monitoring of the cellular growth and differentiation, cytoprotective and immuno-modulatory role.

The local production of calcitriol at the level of the skin results from several successive stages initiated at the level of the epidermis that contains its precursor, the provitamin D. Under the action of the UVB rays, the provitamin D is converted into previtamin D3, itself transformed into vitamin D3 that is then activated at the level of keratinocytes in calcitriol. The thus activated vitamin D is capable of exerting autocrine and paracrine effects by means of a receptor, the vitamin D receptor (VDR). By this method, vitamin D regulates numerous processes involved in cutaneous homeostasis: the formation and maintenance of the epidermal barrier, capillary growth, the innate immune system, and ageing.

The synthesis of vitamin D is under the influence of numerous factors: internal factors such as age or phototype, external factors such as the season, air pollution or the intensity of UV radiation, or else behavioral factors such as wearing clothing, the use of sunscreen, etc. In addition, it is known that insufficient vitamin D is very common and rising steadily, in particular in older individuals and women who are the populations the most at risk.

SUMMARY OF THE INVENTION

The objective of this invention is to propose an active ingredient that promotes the capacity of the skin, in particular aged skin, to stimulate the signaling paths regulated by the VDR by acting like vitamin D.

To this end, the purpose of the invention is the use of particular molecules obtained from the *Cichorium intybus* root.

Bitter chicory or wild chicory or *Cichorium intybus* is an herbaceous plant of the Asteraceae family. Common everywhere, it is easily identified by its terminal and axial clusters of fully ligulate blue flowers. It is originally from Europe, and temperate regions of Asia and North Africa, and it is naturalized in. North America.

Chicory is extensively cultivated for its use for fodder and food. Its above-ground parts are consumed in salads. Since the middle of the eighteenth century, the roots harvested in autumn are roasted to be used as a coffee substitute.

Chicory is also conventionally used for its choleretic, cholagogue, diuretic, depurative and digestive medicinal qualities.

*Cichorium intybus* extracts have further been used in cosmetic products, in particular for a pigmenting effect in the application EP-1,707,191 or EP-2,277,502, an anti-inflammatory effect in the application EP-1,962,875, an anti-radical effect for preventing cutaneous ageing in the application FR-2,626,469, or else in a mixture with other plants in thinning or softening cosmetic products.

The purpose of this invention is specifically the cosmetic use of a *Cichorium intybus* root hydrolyzate comprising oligofructosans as an active ingredient in a composition with cutaneous application, for acting in a way similar to vitamin D on the cells of the skin, in particular for stimulating the signaling paths regulated by the vitamin D receptor in the cutaneous cells.

Actually, in a surprising way, using oligofructosans obtained by *Cichorium intybus* root hydrolysis on the skin makes it possible to restore the functionality of the VDR in the cells of the skin of individuals that are apt to have a vitamin D deficiency and by this mechanism to stimulate the molecular network involved in the terminal differentiation of keratinocytes and to promote the formation of the cutaneous barrier.

In a specific way, the purpose of the invention is also a particular cosmetic active ingredient, namely a *Cichorium intybus* root hydrolyzate that comprises oligofructosans.

"Hydrolyzate" is defined as any extract that is obtained from the *Cichorium intybus* root, comprising at least one hydrolysis stage, preferably at least one enzymatic hydrolysis stage.

Finally, the invention also has as its object a cosmetic composition that contains this active ingredient, as well as a cosmetic treatment process designed to preserve the integrity or to promote recovery of the barrier function of the skin comprising the topical application of such a composition.

BRIEF DESCRIPTION OF DRAWINGS

This invention is now described in detail relative to the accompanying figures in which.

DETAILED DESCRIPTION OF THE INVENTION

Use

Figure 1A:
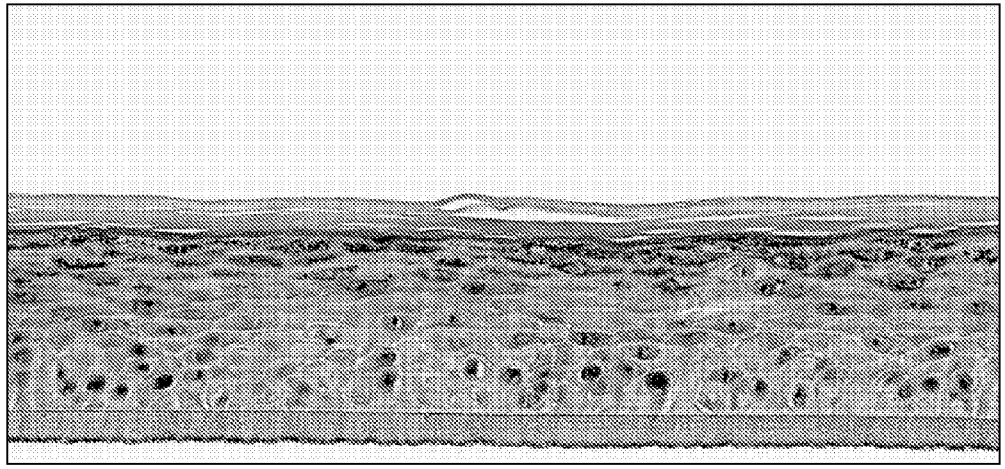
FIGS. 1a to 1d show the images obtained for the results of the study A.III on the thickness of the epidermis on D19:
1a Young reconstructed epidermis control,
1b Aged reconstructed epidermis control,
1c Aged reconstructed epidermis+$10^{-8}$M calcitriol,
1d Aged reconstructed epidermis+Example 10.5% active ingredient.

According to a first aspect, the purpose of the invention is a *Cichorium intybus* root hydrolyzate comprising oligofructosans for its application as an active ingredient in a composition with cutaneous application, with said active ingredient and/or said composition being designed to act in a way similar to vitamin D in the cells of the skin, in particular for a cutaneous restructuring effect. Applied on the skin, the active ingredient and/or the composition make(s) it possible in particular to stimulate the synthesis of the vitamin D receptor (VDR) and/or to increase the functionality of the VDR in the cutaneous cells and to stimulate the network of genes engaged in the terminal differentiation of keratinocytes, regulated by the VDR.

The best-known mode of action of vitamin D involves the activation of its specific nuclear receptor, the VDR, which regulates the expression of target genes.

On the cutaneous level, the VDR is expressed in relation to keratinocytes, fibroblasts, melanocytes, Langerhans cells, macrophages, as well as endothelial cells, which contributes to the varied cellular effects of vitamin D.

The VDR level is an important parameter in the biological response of vitamin D. The more elevated it is, the higher the transcriptional activity of the activated target genes.

According to the invention, the use of a *Cichorium intybus* root hydrolyzate comprising oligofructosans on the skin makes it possible to stimulate the synthesis of the vitamin D receptor (VDR) and/or to increase the functionality of the VDR in the cutaneous cells, thus acting in a way that is similar to vitamin D.

It is also known that vitamin D and its receptor regulate numerous central processes involved in the homeostasis of the epidermis, in particular the key stages that end in the formation of an optimal and functional barrier function.

The epidermis is a multi-stratum epithelium composed of cells having a morphology that is specific to each layer. The epidermis renews itself by cellular division starting from basal cells and then by differentiation of the keratinocytes into corneocytes. During their migration toward the surface of the skin, the keratinocytes undergo biochemical and structural modifications to be transformed gradually into corneocytes. The terminal differentiation of the corneocyte involves the formation of an intracorneocytic fibrous matrix, the production of intercellular lipids, and the appearance of a cornified envelope leading to the formation of the stratum corneum. The corneocytes are ultimately eliminated thanks to the desquamation process that makes possible renewal of the epidermis and maintenance of its thickness.

The three stages of differentiation, cornification and desquamation are essential to the integrity of the epidermis and to the formation of its functional barrier. The VDR is at the center of the network of genes that regulate these stages:

It stimulates the Kruppel-like factor (KLF4 factor of Kruppel-4 type), transcription factor that orchestrates the development of the epidermal barrier by controlling the expression of the markers of terminal differentiation, It increases the expression of cytokeratins 1 and 10 as well as that of involucrin and the transglutaminase, and it thus accelerates the process of differentiation and maturation of the cornified envelope, It controls the expression of protease inhibitors such as cystatin E/M. Cystatin E/M, inhibitor of lysosomal protease cysteines, plays a role, on the one hand, in the terminal differentiation of keratinocytes by indirectly inhibiting the activity of transglutaminases that make possible the connection of the structural proteins of the cornified envelope. On the other hand, it controls the desquamation process by limiting the activity of the cathepsin V.

It stimulates the expression of kallikreins (KLK), which are serine proteases involved in the desquamation process, in particular the KLK5 or KLK7 that are responsible for the degradation of intercorneocytic bonds composed of desmoglein-1, desmocollin-1, as well as corneodesmosin.

According to the invention, the use of a *Cichorium intybus* root hydrolyzate comprising oligofructosans on the skin makes it possible to stimulate the signaling paths that are regulated by the vitamin D receptor in the cutaneous cells, in particular to increase the expression of KLF4, cytokeratin 1, involucrin, cystatin E/M and/or KLK5. It thus stimulates the network of genes engaged in the terminal differentiation of keratinocytes and promotes the formation of the cutaneous barrier.

The invention is particularly suitable for skin that is apt to have a vitamin D deficiency, in particular aged skin. It is actually known that the level of vitamin D in the skin varies and depends on numerous factors. In particular, several studies have shown a decline relative to the age of the cutaneous synthesis of vitamin D and tissue responses that are induced.

In addition, the applicant demonstrated that the aged human keratinocytes have a reduced capacity to synthesize the vitamin D receptor (VDR) in comparison to young human keratinocytes.

Also, by acting in a way that is similar to vitamin D, a *Cichorium intybus* root hydrolyzate that comprises oligofructosans applied on the skin makes it possible to restore the endogenous capacity of aged cells to stimulate the signaling paths regulated by the VDR. It thus reinforces the cutaneous barrier and improves the capacity for recovery of the skin of mature individuals, apt to have a vitamin D deficiency.

According to a particularly suitable embodiment, the purpose of the invention is the use of a *Cichorium intybus* root hydrolyzate that comprises oligofructosans as described below.

Active Ingredient

The invention also relates to a particular cosmetic active ingredient, namely a *Cichorium intybus* root hydrolyzate comprising oligofructosans, preferably oligofructosans with a degree of polymerization that is between 3 and 20.

According to a particularly suitable embodiment:
The total sugars represent at least 46% by weight of the dry material of the active ingredient, and/or
The oligofructosans represent at least 69% by weight of total sugars of the active ingredient.

In a preferred way, the oligofructosans represent at least 31% by weight of dry material of the active ingredient.

The active ingredient according to the invention is preferably an enzymatic hydrolyzate.

The active ingredient preferably has a clear yellow color.

It can come in liquid form and be defined by at least one, preferably all, of the characteristics disclosed below.

Dry Materials:

The level of dry materials of an active ingredient according to the invention (measured by running a sample with a given initial weight through the oven at 105° C. in the presence of sand until a constant weight is obtained) can be between 30 and 90 g/l, preferably between 45 and 65 g/l.

Measurement of the pH:

The pH (measured by the potentiometric method at ambient temperature) can be between 3.5 and 6.5, preferably between 4.5 and 5.5.

Carbohydrates:

Determination of the Total Sugar Content

The metering of the total sugar content can be done by the DUBOIS method (DUBOIS, M. et al., (1956), Analytical Chemistry, 28, No. 3, pp. 350-356). In the presence of concentrated sulfuric acid and phenol, the reducing sugars provide an orangey-yellow compound. Starting from a standard range, it is possible to determine the level of total sugars of a sample. The total sugar content can be between 20 and 62 g/l, preferably between 30 and 45 g/l.

The total sugar content is preferably greater than or equal to 46% by weight of dry material.

Characterization of the Carbohydrate Fraction:

The determination of the size of carbohydrates of an active ingredient according to the invention is made by high-performance liquid chromatography.

The chromatogram that is obtained shows the presence of between 10 and 31% of monosaccharides of a molecular weight that is less than 180 Da and of between 69 and 90% of oligosaccharides with a molar weight of between 180 and 5,900 Da (maximum degree of polymerization of 33).

The characterization of carbohydrates of the active ingredient by HPLC chromatography shows that the sugars of the active ingredient according to the invention have a degree of polymerization of between 3 and 20 for at least 69% of the oligosaccharides.

Furthermore, the analysis of the composition of simple sugars of the active ingredient according to the invention shows that it essentially consists of fructose in bound form.

The glucidic fraction of the active ingredient according to the invention therefore consists essentially of oligofructosans with a degree of polymerization of between 3 and 20.

Content of Raw Ashes:

The content of raw ash is determined by weighing the residues obtained from incineration at 550° C. in an electric muffle furnace (VULCAN™).

The weight of the residue is calculated by subtracting the tare.

The mineral content is expressed in terms of percentage relative to the total weight of the dry material of the active ingredient.

The content of raw ashes of an active ingredient according to the invention is preferably between 7.9 and 9.7%.

Content of Uronic Acids:

The product of galacturonic acid with sodium tetraborate provides, in the presence of meta-hydroxydiphenyl, a rose coloring that makes possible spectrophotometer metering at 520 nm.

The coloring intensity is proportional to the quantity of uronic acids.

The readings are done starting from a standard range of galacturonic acid ranging from 10 to 100 mg/l.

The results that are obtained for the standards make it possible to trace an optical density straight line based on the concentration, and the level of uronic acids of the samples is read directly on this straight line.

The content of uronic acids of an active ingredient according to the invention can be between 9.3 and 11.5% by weight relative to the dry material.

Proteins:

The total nitrogen content is determined by the KJELDHAL method; it represents the protein content.

The protein content of an active ingredient according to the invention is preferably between 4.2 and 5.2% by weight relative to the dry material.

Furthermore, the characterization of the protein fraction of the active ingredient according to the invention carried out by FPLC shows that for the most part, it consists of peptides that have a molecular weight that is less than 2,000 Da.

Phenolic Compounds:

The metering of the phenolic compounds is done by reading the coloring intensity in the presence of potassium ferricyanide, an intensity that can be detected at 715 nm and compared to a standard range of gallic acid.

The level of polyphenols is less than 0.05% of the dry material.

The active ingredient according to the invention does not contain polyphenolic compounds.

Identification of the Active Fraction

So as to demonstrate that the fraction that is for the most part active of the active ingredient according to the invention is indeed the fraction that consists of oligofructosans, a study was done. This study consists in fractionating the primary molecular radicals of the active ingredient according to the invention:

A fraction A, composed of ashes, obtained by re-dissolving residues obtained from incineration at 550° C. in an electronic muffle furnace, recovered in distilled and filtered water, A fraction B containing 98% of the carbohydrates of the active ingredient, and a very small quantity of proteins.

The study consists in comparing the effect of these different fractions on the expression of the involucrin and the KLK5 by quantitative PCR on normal human keratinocytes, with the result obtained for the active ingredient according to the invention at 1%. The test protocol is the one described in Item II. The results that are obtained are presented in the table below:

|  | Expression of RNAm (%) | |
| --- | --- | --- |
|  | Involucrin | KLK5 |
| Control | 100 | 100 |
| Example 1 1% Active Ingredient | 151 | 122 |
| 1% Fraction A | 68 | 69 |
| 1% Fraction B | 138 | 126 |

Fraction A is not effective. It is fraction B that imparts its activity to the active ingredient.

The analysis of fraction B by HPLC (High-Performance Liquid Chromatography) shows that it consists of oligofructosans with a degree of polymerization that for the most part is between 3 and 20.

These are therefore indeed the oligofructosans, in particular the oligofructosans with a degree of polymerization of between 3 and 20, which impart its effectiveness to the active ingredient.

Production Process

The active ingredient according to the invention as described above is obtained by a process that comprises a hydrolysis stage, preferably an enzymatic hydrolysis.

A particularly suitable process comprises at least the series of following stages:

Dissolving *Cichorium intybus* root powder in water,
Enzymatic hydrolysis,
Separation of soluble and insoluble phases for recovering the soluble phase,
Enzymatic inactivation by heat treatment,
Preferably filtration and recovery of filtrate,
Purification and concentration of the active fraction,
Preferably filtration and/or sterilizing filtration and recovery of the filtrate.

The stages of deodorization and color removal can be added.

The parameters of the different stages should be adjusted so as to obtain active ingredients comprising oligofructosans, preferably oligofructosans with a degree of polymerization of between 3 and 20, in particular an active ingredient in which the oligofructosans represent at least 69% by weight of total sugars of the active ingredient.

Compositions and Cosmetic Skin-Care Process

This invention also covers the compositions, in particular the cosmetic compositions, including a *Cichorium intybus* root hydrolyzate comprising oligofructosans, in different galenical forms, suitable for administration by cutaneous topical means.

These compositions can come in particular in the form of oil-in-water emulsions, water-in-oil emulsions, multiple emulsions (water/oil/water or oil/water/oil) that can optionally be microemulsions or nanoemulsions, or in the form of solutions, suspensions, hydrodispersions, aqueous gels or powders. They can be more or less fluid and have the appearance of a cream, a lotion, a milk, a serum, an ointment, a gel, a paste, or a foam, or they can be in solid form.

These can be compositions comprising between 0.01 and 3% of active ingredient(s) obtained according to this invention.

These compositions comprise, in addition to the active ingredient, a physiologically acceptable and preferably cosmetically acceptable medium, i.e., that does not cause sensations of unacceptable discomfort for the user such as redness, tingling, or stinging.

The compositions according to the invention can contain as adjuvant at least one compound that is selected from among:
  Oils, which can be selected in particular from among volatile or non-volatile, linear or cyclic, silicone oils;
  Waxes, such as ozokerite, polyethylene wax, beeswax or carnauba wax;
  Silicone elastomers,
  Surfactants, preferably emulsifying surfactants, whether they are non-ionic, anionic, cationic or amphoteric;
  Co-surfactants, such as linear fatty alcohols;
  Thickeners and/or solidifiers,
  Moisturizers, such as polyols like glycerin;
  Organic filters,
  Inorganic filters,
  Dyes, preservatives, feedstocks,
  Tightening agents,
  Sequestering agents,
  Perfumes,
  And mixtures thereof, without this list being limiting.

Examples of such adjuvants are cited in particular in the CTFA Dictionary (International Cosmetic Ingredient Dictionary and Handbook published by the Personal Care Product Council).

Of course, one skilled in the art will make sure to select possible active or non-active complementary compounds and their quantities in such a way that the advantageous properties of the mixture are not, or essentially are not, altered by the addition being considered.

These compositions are designed in particular to act in a way that is similar to vitamin D on the cells of the skin, in particular:
  To stimulate the signaling paths regulated by the vitamin D receptor in the cutaneous cells,
  To stimulate the synthesis of the vitamin D receptor and/or to increase the functionality of the vitamin D receptor in the cutaneous cells,
  To stimulate the network of genes engaged in the terminal differentiation of the keratinocytes,
  To increase the expression of KLF4, cytokeratin 1, involucrin, cystatin E/M and/or KLK5 in the cutaneous cells,
  To promote the formation of the epidermal barrier.

These compositions are therefore essentially designed to preserve the integrity or to promote recovery of the barrier function of the skin, in particular on skin that may have a vitamin D deficiency such as the aged skin.

The object of the invention is therefore also for this purpose a cosmetic process for care of the human skin, designed to preserve the integrity or to promote recovery of the barrier function of the skin, comprising the topical application of a composition that contains a *Cichorium intybus* root hydrolyzate comprising oligofructosans.

EXAMPLES

A nonlimiting example of the production process and the active ingredient containing oligofructosans obtained by hydrolysis starting from the *Cichorium intybus* root is presented below, as well as composition examples including such an active ingredient.

Example 1

Active Ingredient According to the Invention

An example of a process for obtaining an active ingredient according to the invention comprises the implementation of the following stages:
  Dissolving *Cichorium intybus* root powder in water at a rate of 50 g/l at 50° C. for 3 hours,
  Enzymatic hydrolysis using a carbohydrase,
  Separation of the soluble and insoluble phases by decanting to recover the soluble phase,
  Enzymatic inactivation by heat treatment,
  Filtering and recovery of the filtrate,
  Purification and concentration of the active fraction,
  Color removal,
  Sterilizing filtration.

The active ingredient that is obtained has the following characteristics:
  Appearance: clear liquid
  Color: clear yellow
  Content of dry materials: 60.8 g/l
  pH: 4.9
  Total sugar content: 46.3 g/l, or 76.1% by weight relative to the dry material, of which 77% is in oligofructosan form,
  Total protein content: 4.7% by weight relative to the dry material,
  Uronic acid content: 10.4% by weight relative to the dry material,
  Ash content: 8.8% by weight relative to the dry material,
  Polyphenol content: 0.01% by weight relative to the dry material.

Example 2

Use of an Active Ingredient According to the Invention in a Matting Gel

| Phase A. | Water | Enough to make 100% |
|---|---|---|
| | Glycerol | 6% |
| | Carbopol Ultrez 20 | 0.5% |

-continued

| Phase B. | Lanol 1688 (Seppic) | 3% |
| --- | --- | --- |
| | Montanov (Seppic) | 2% |
| | Sophiderm (Sophim) | 3% |
| | Patlac ISL (Rita) | 2% |
| | DUB 1632 (Stéarinerie Dubois) | 4% |
| | DUB MCT5545 (Stéarinerie Dubois) | 4% |
| Phase C. | Active ingredient according to the invention (Example 1) | 3% |
| | Preservative | 0.7% |
| Phase D. | NaOH | Enough to make pH 6 |

The quantities that are indicated are provided in percentage by weight.

This compact white emulsified gel has a pH of 6. In topical application, it has an agreeable touch and leaves a soft film.

It can be obtained by the implementation of the following stages:
- Mixing A, and heating in a water bath at 80° C. while being stirred magnetically and while ensuring good dispersion of the gel,
- Mixing B, and heating in a water bath at 80° C. while being stirred magnetically,
- Emulsifying B in A with a rotor-stator at 2,000 rpm,
- At 60° C., adding C in order, still with a rotor-stator at 2,000 rpm,
- At 30° C., adjusting with D, while being stirred mechanically at 1,200 rpm,
- Allowing to cool, while being stirred, to control the homogenization of the cream.

Example 3

Use of an Active Ingredient According to the Invention in a Hydrating Cream

| Phase A. | Water | Enough to make 100% |
| --- | --- | --- |
| | Butylene glycol | 4.3% |
| Phase B. | Montanov 14 (Seppic) | 4% |
| | Cetearyl alcohol | 3% |
| | DUB SEG (Stéarinerie DUBOIS) | 3% |
| | DUB Lilirose (Stéarinerie DUBOIS) | 3% |
| | DUB Aprilose (Stéarinerie DUBOIS) | 3% |
| | Montanov 68 (Seppic) | 3% |
| Phase C. | Active ingredient according to the invention (Example 1) | 3% |
| | Preservative | 0.7% |

The quantities that are indicated are provided in percentage by weight.

This white and compact emulsion has a pH of 6.5. In topical application, it has a velvety touch with a soft finish and a homogeneous effect.

It can be obtained by the implementation of the following stages:
- Mixing A, heating in a water bath at 80° C. while being stirred magnetically and while ensuring good dispersion of the gel,
- Mixing B, heating in the water bath at 80° C. while being stirred magnetically,
- Emulsifying B in A with a rotor-stator emulsifier at 3,000 rpm,
- At 40° C., adding C in order with a rotor-stator at 3,000 rpm,
- Leaving it to stir until homogenization is complete.

Example 4

Use of an Active Ingredient According to the Invention in an Emulsion

| Phase A. | Water | Enough to make 100% |
| --- | --- | --- |
| | Glycerol | 6.7% |
| | Satialgine US 551 (Degussa) | 2% |
| Phase B. | Montanov 68 (Seppic) | 2% |
| | Montanov S (Seppic) | 1% |
| | Pelemol BB (Phoenix Chemical) | 2% |
| | Pelemol 2014 (Phoenix Chemical) | 3% |
| | Sophim MC30 (Sophim) | 3.5% |
| | DUB MCT 5545 (Stéarinerie Dubois) | 3% |
| | DUB Aprilose (Stéarinerie Dubois) | 2.6% |
| | DUB OK18 (Stéarinerie Dubois) | 3.5% |
| | DUN IPP (Stéarinerie Dubois) | 4% |
| Phase C. | Preservative | 0.7% |
| | Active ingredient according to the invention (Example 1) | 3% |

The quantities that are indicated are provided in percentage by weight.

This smooth beige emulsified gel has a pH of 5. In topical application, it has a fast penetration with a soft and dry finish.

It can be obtained by the implementation of the following stages:
- Mixing A, dispersing the gel in the water bath at 80° C. while being stirred magnetically at 1,000 rpm,
- Mixing B, heating in a water bath at 80° C. while being stirred magnetically,
- Emulsifying B in A with a rotor-stator at 1,700 rpm,
- At 40° C., adding C in the order indicated with a rotor-stator at 1,800 rpm,
- At 30° C., slowly adding D to adjust the pH while being stirred between 1,000 and 1,500 rpm and leaving it to stir until homogenization is complete.

Example 5

Use of an Active Ingredient According to the Invention in a Serum

| Phase A. | Water | Enough to make 100% |
| --- | --- | --- |
| | Carbopol 940 (Lubrizol) | 0.3% |
| | Glycerol | 6% |
| Phase B. | Simulsol 220 TM (Seppic) | 6.7% |
| | Sterol CC9595 (Alpinia) | 6.7% |
| | Eucarol D (Alpinia) | 3% |
| Phase C. | Active ingredient according to the invention (Example 1) | 3% |
| | Preservative | 0.7% |
| Phase C. | NaOH | Enough to make pH 7 |

The indicated quantities are provided in percentage by weight.

This transparent liquid emulsified gel has; a pH of 7. In topical application, it has a comfortable touch with a dry finish and a mat effect. It can be obtained by the implementation of the following stages:
- Mixing A, heating in a water bath at 80° C. while being stirred magnetically and while ensuring good dispersion of the gel,
- Mixing B, heating in a water bath at 80° C. while being stirred magnetically, Emulsifying B in A with a rotor-stator at 1,000 rpm,
At 30° C., adding C, in the order indicated, and adjusting the pH, with D, slowly with a rotor-stator at 1,000 rpm, and continuing the stirring until homogenization is complete.

Example 6

Use of an Active Ingredient According to the Invention in a Daily Cream

| Phase A. | Water | Enough to make 100% |
|---|---|---|
| | Butylene glycol | 3.5% |
| Phase B. | DC 73 100 (Dow Corning) | 4% |
| | Diamant N (Aiglon) | 4% |
| | Simulsol M45 (Seppic) | 4% |
| | DUB RG AE (Stéarinerie Dubois) | 3.5% |
| | PEG 4000 stearate (Stéarinerie Dubois) | 2% |
| | Lanol 14 M (Seppic) | 2% |
| | DUB MM (Stéarinerie DUBOIS) | 2% |
| | Pelemol 2014 (Phoenix Chemical) | 2% |
| | Montanov 14 (Seppic) | 3% |
| Phase C. | Active ingredient according to the invention (Example 1) | 3% |
| | Preservative | 0.7% |

The quantities that are indicated are provided in percentage by weight.

This white and fluid emulsion has a pH of 4.7. In topical application, it has an easy and film-forming penetration.

It can be obtained by the implementation of the following stages:
Mixing A, heating in a water bath at 80° C. while being stirred magnetically,
Mixing B, heating in a water bath at 80° C. while being stirred magnetically,
Emulsifying B in A with a rotor-stator emulsifier at 1,500 rpm,
At 30° C., adding C in order with a rotor-stator at 1,500 rpm, and continuing the stirring until cooling is completed.

Example 7

Use of an Active Ingredient According to the Invention in an Emulsified Gel

| Phase A. | DUB GC7 (Stéarinerie Dubois) | 1.2% |
|---|---|---|
| | DUB MCT 5545 (Stéarinerie Dubois) | 0.8% |
| | CARBOPOL ETD2020 (Novéon) | 0.2% |
| | Preservative | 0.7% |
| Phase B. | Active ingredient according to the invention (Example 1) | 3% |
| Phase C. | NaOH | Sufficient quantity, pH 6.3 |
| Phase D. | Water | Enough to make 100% |

The quantities that are indicated are provided in percentage by weight.

This emulsified gel has a pH of 6.3. It can be obtained by the implementation of the following stages:
Mixing A and heating in a water bath at 45° C.,
Homogenizing A while being stirred mechanically until dispersion of the gel is completed,
Adding B with a graduated pipette,
Adjusting the pH slowly with C with a pastette by adapting the stirring to the viscosity of the product.

Evaluation of the Cosmetic Effectiveness of an Active Ingredient According to the Invention A. In-Vitro Tests I. Study of the Effect on the Functionality of the Vitamin D Receptor With vitamin D in its active form (calcitriol) being central in the regulation of a network of genes dedicated to the control of the terminal epidermal differentiation, it seems advantageous to identify the functionality of the vitamin D receptor (VDR) of aged skin by comparison to young skin and to evaluate the effect of the active ingredient according to the invention on the VDR.

The first objective of this study is to compare the synthesis of VDR between human keratinocytes obtained from young donors (of an age of less than 30 years) and keratinocytes that are obtained from aged donors (of an age of greater than 60 years).

The second objective is to evaluate the effect of a *Cichorium intybus* root hydrolyzate comprising oligofructosans (Example I) on its capacity to increase the synthesis of VDR of human keratinocytes obtained from aged donors (age of greater than 60 years).

The study was done by Western Blot, and the operating procedure is described below.

On D0, the human keratinocytes of young donors and aged donors are inoculated and incubated at 37° C.

On D2, the cells are treated with the active ingredient of Example 1 at 0.5%, 1% and 2% (V/V) or with $10^{-7}$M calcitriol (positive control). The cells are next incubated for 24 hours at 37° C.

On D3, the cellular extracts are recovered and then metered by Western blot.

The results that are obtained are presented below:

| | VDR Level (UA) | VDR Level/Young Control (%) | VDR Level/Aged Control (%) |
|---|---|---|---|
| Young Keratinocytes | | | |
| Control | 0.229 | — | |
| Example 1 1% Active Ingredient | 0.276 | +20 | |
| Example 1 2% Active Ingredient | 0.293 | +28 | |
| Aged Keratinocytes | | | |
| Control | 0.162 | −29 | — |
| $10^{-7}$M Calcitriol | 0.214 | | +31 |
| Example 1 0.5% Active Ingredient | 0.196 | | +21 |
| Example 1 1% Active Ingredient | 0.215 | | +32 |
| Example 1 2% Active Ingredient | 0.221 | | +36 |

First of all, these results show that the synthesis of the vitamin D receptor is significantly reduced (29% under the conditions of this study) in the aged human keratinocytes compared to that of young human keratinocytes.

In addition, it is noted that a *Cichorium intybus* root hydrolyzate comprising oligofructosans makes it possible to increase the synthesis of the vitamin D receptor on human keratinocytes. In particular, in aged human keratinocytes, the active ingredient of Example 1 according to the invention that is tested at 1% makes it possible to increase the synthesis of the vitamin D receptor by 32%.

Finally, it is also noted that the *Cichorium intybus* root hydrolyzate comprising oligofructosans has an effect that is similar to the one that is obtained with calcitriol.

II. Study of the Effect on the Molecular Network Involved in the Terminal Differentiation of Keratinocytes The object of this study is to evaluate the effect of a *Cichorium intybus* root hydrolyzate comprising oligofructosans (Example 1) on its capacity to modulate the expression of the RNAm coding for epidermal differentiation proteins:

Kruppel-like factor 4 (KLF4): transcription factor involved in the terminal differentiation of keratinocytes,
Cytokeratin 1 (CK1): components of intermediate keratin filaments,
Involucrin: protein of the cornified envelope,
Cystatin E/M: Inhibitor of lysosomal protease cysteines that are involved in the differentiation of keratinocytes and desquamation.
Kallikrein 5 (KLK5 or SCTE): stratum corneum tryptic enzyme involved in desquamation.

The study was done by quantitative PCR on normal human keratinocytes obtained from aged donors (age of greater than 60 years), according to the operating procedure described below.

On D0, the human keratinocytes of aged donors are inoculated and incubated at 37° C.

On D2, the cells are treated with the Example 1 0.5%, 1% and 2% active ingredients (V/V) or with $10^{-7}$M calcitriol (positive control). The cells are then incubated for 48 hours at 37° C.

On D4, the cells are recovered, and the total RNA are extracted. The RNA are reverse-transcripts, and the complementary DNA that are obtained are analyzed by quantitative PCR (quantitative polymerase chain reaction).

The quantification of the incorporation of fluorescence is measured continuously using a thermal cycler, and the relative quantification is carried out using software.

The results that are obtained are presented in the table below:

|  | RNAm Level/Control (%) | | | |
| --- | --- | --- | --- | --- |
|  | Active Ingredient (Example 1) | | | $10^{-7}$M |
|  | 0.5% | 1% | 2% | Calcitriol |
| Cytokeratin 1 | +41 | +72 | +165 | 0 |
| Involucrin | +40 | +51 | +81 | +42 |
| KLF4 | +8 | +22 | +8 | +25 |
| Cystatin E/M | +29 | +41 | +57 | +65 |
| KLK5 | +19 | +22 | +23 | +26 |

These results show that in aged human keratinocytes, a *Cichorium intybus* root hydrolyzate comprising oligofructosans significantly increases the expression of genes involved in the epidermal terminal differentiation.

It is also noted that the effect of the *Cichorium intybus* root hydrolyzate comprising oligofructosans is comparable to the one that is obtained with calcitriol.

III. Study of the Effect on the Formation of the Cutaneous Barrier

The object of this study is to evaluate the capacity of a *Cichorium intybus* root hydrolyzate comprising oligofructosans to promote the construction of a stratified and functional epidermis starting from aged human keratinocytes obtained by successive replications.

The operating procedure is described below.

First, the young human keratinocytes (passage 1: P1) are cultivated and replicated up to passage 5 (P5) in a specific culture medium (CnT-57) that may or may not contain the Example 1 0.5% active ingredient or $10^{-8}$M calcitriol (positive control).

Next, the reconstructed epidermis (RE) is obtained after the young or aged human keratinocytes are cultivated.

On D12 and D19, the RE are recovered, fixed, dehydrated and included in paraffin. Sections (4 μm) are then made using a microtome.

Next, an HE coloring, and then an immunohistological marking of the filaggrin, terminal differentiation marker, are carried out.

The display is produced on a microscope coupled with an image analysis system:

The thickness of the epidermis (living cell layers) is measured on the histological sections after the HE coloring,
The synthesis of the filaggrin is proportional to the intensity of the fluorescence (green color) that is present in the reconstructed epidermis.

Figure 1B:
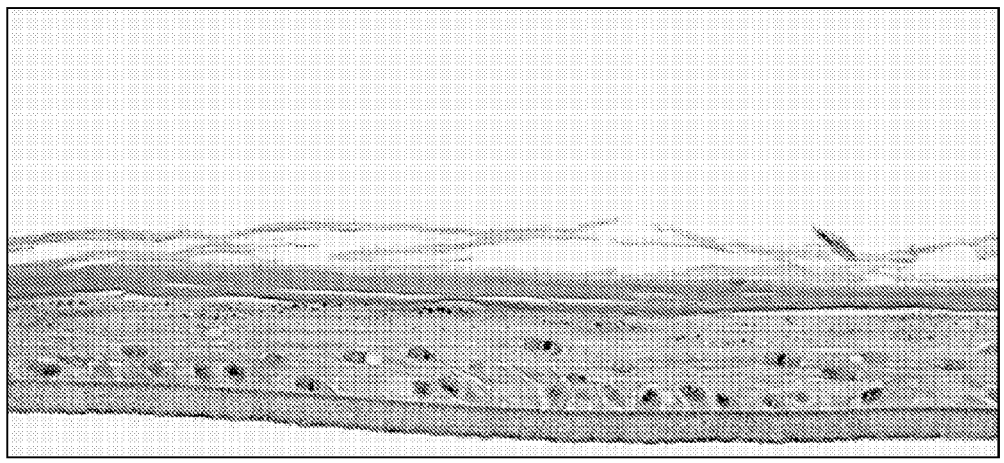
Figure 1C:
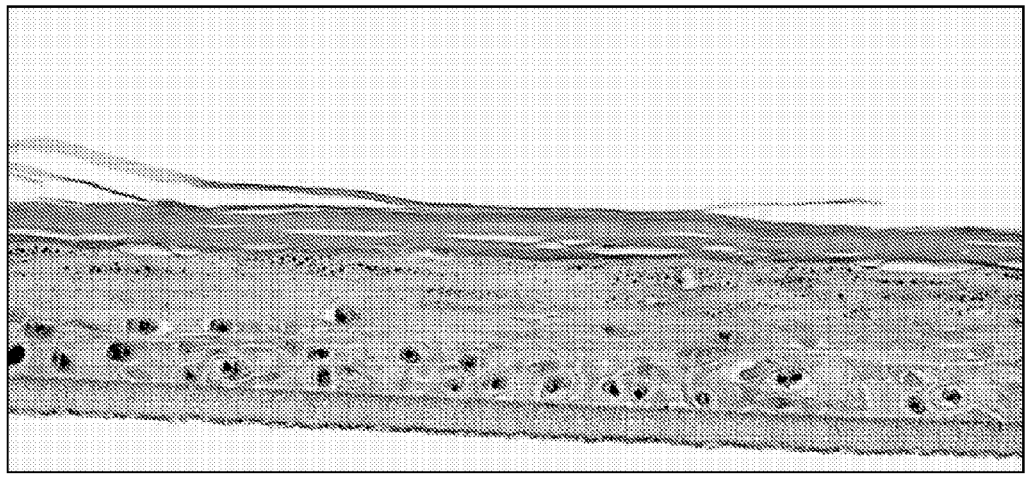
Figure 1D:
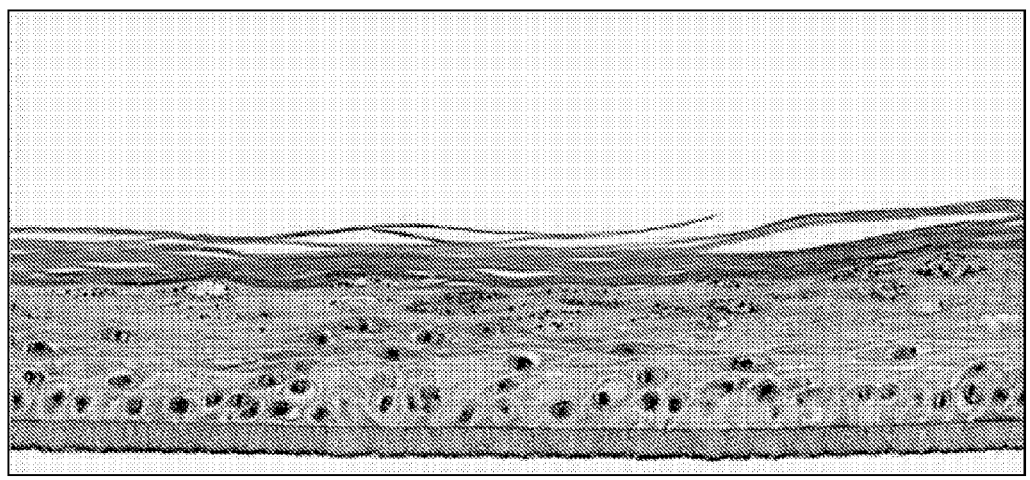
Figure 2A:
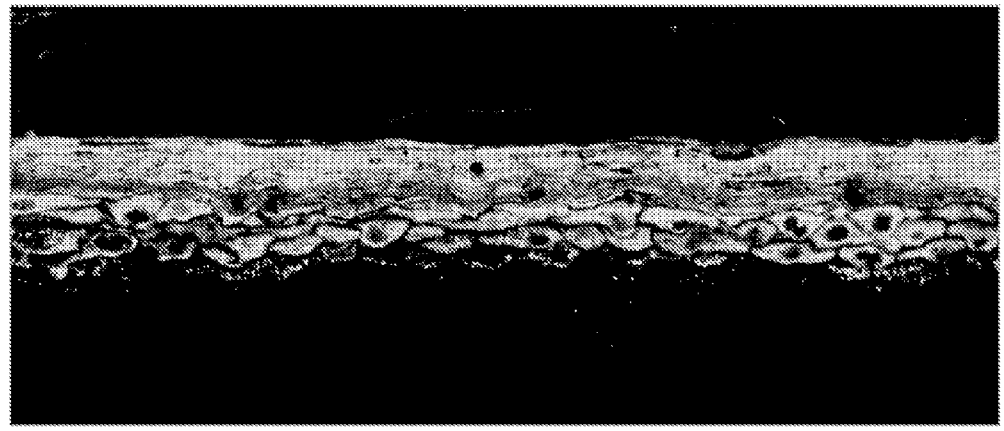
FIGS. 2a to 2d show the images that are obtained for the results of study A.III on the synthesis of filaggrin on D19:
2a Young reconstructed epidermis control,
2b Aged reconstructed epidermis control,
2c Aged reconstructed epidermis+$10^{-8}$M calcitriol,
2d Aged reconstructed epidermis+Example 10.5% active ingredient.
Figure 2B:
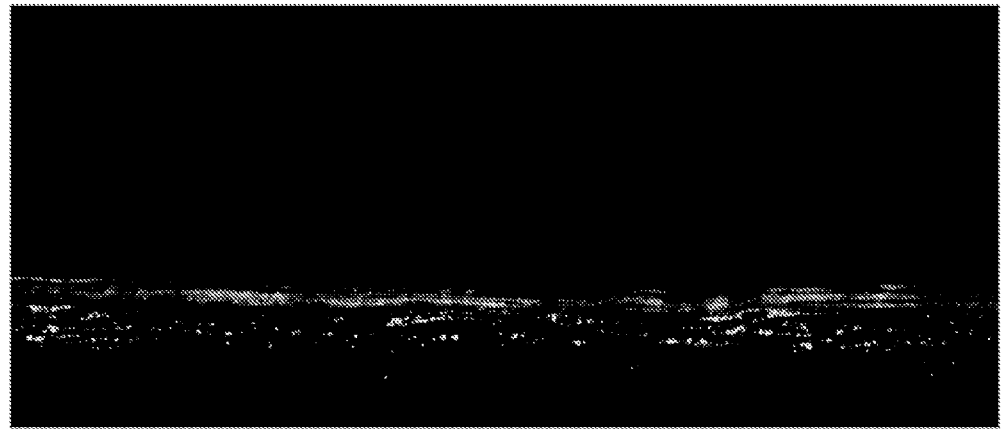
Figure 2C:
Figure 2D:
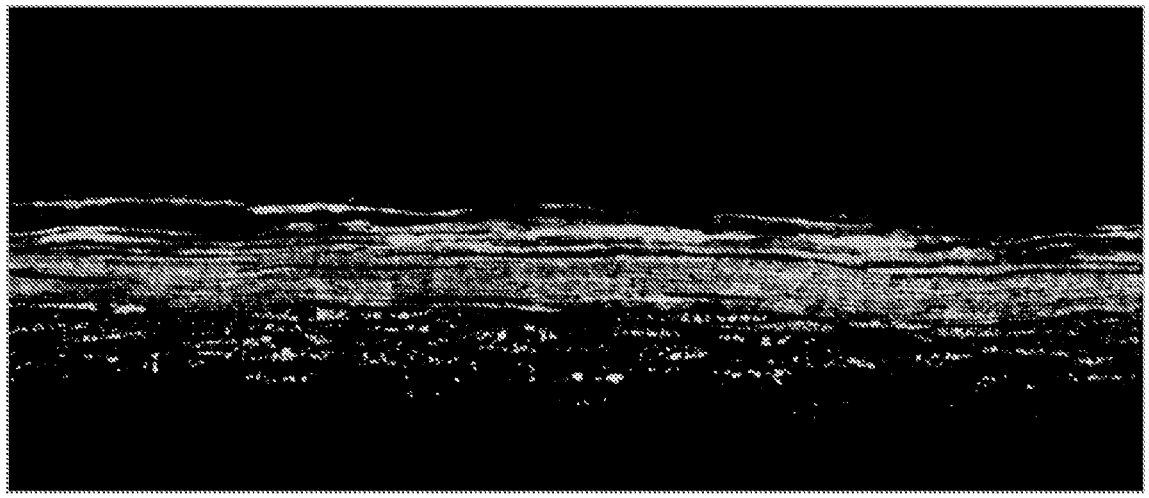

The results that are obtained are presented in the two tables below as well as in FIGS. 1*a* to 1*d* and 2*a* to 2*d* for the results on D19:

|  | Thickness of the Epidermis (μm) | |
| --- | --- | --- |
|  | D12 | D19 |
| Young Reconstructed Epidermis | | |
| Control | 46.4 | 72.6 (FIG. 1a) |
| Aged Reconstructed Epidermis | | |
| Control | 29.6 | 43.2 (FIG. 1b) |
| $10^{-8}$M Calcitriol | 37.8 | 58.6 (FIG. 1c) |
| Example 1 0.50% Active Ingredient | 40.2 | 54.2 (FIG. 1d) |

|  | Synthesis of Filaggrin ($\times 10^4$ UA) | |
| --- | --- | --- |
|  | D12 | D19 |
| Young Reconstructed Epidermis | | |
| Control | 137 | 1472 (FIG. 2a) |
| Aged Reconstructed Epidermis | | |
| Control | 41 | 354 (FIG. 2b) |
| $10^{-8}$M Calcitriol | 116 | 795 (FIG. 2c) |
| Example 1 0.50% Active Ingredient | 196 | 897 (FIG. 2d) |

First of all, it is noted that the quality and the functionality of the epidermis constructed starting from aged human keratinocytes are altered relative to those of the epidermis constructed starting from young human keratinocytes.

It is also noted that the pretreatment of aged keratinocytes with a *Cichorium intybus* root hydrolyzate comprising 0.50% oligofructosans makes it possible to increase the thickness of the epidermis and the synthesis of filaggrin.

These results therefore show well that a *Cichorium intybus* root hydrolyzate comprising oligofructosans improves the capacity of the aged human keratinocytes in order to construct a stratified and functional epidermis.

IV. Study of Anti-Radical Activity

This study has as its object to evaluate the anti-radical activity of a *Cichorium intybus* root hydrolyzate comprising oligofructosans according to the DPPH (diphenyl picrylhydrazyl hydrate) method.

The DPPH is a free radical that absorbs in the violet at 517 nm. An anti-radical product brings about a disappearance of the violet coloring.

The DPPH solution that is used for this study is a solution that is prepared starting from 4.8 mg of DPPH dissolved in methanol.

The procedure of the study is described below.

The DPPH solution and the Example 1 10% and 20% active ingredients or distilled water (for the control) are added to the hemolysis tubes.

It is stirred, and a waiting period of 20 minutes is observed before the optical densities at 517 nm are read against air.

The results that are obtained are presented in percentage of anti-radical activity in the table below:

| Metering of Example 1 Active Ingredient | Anti-Radical Activity |
|---|---|
| 10% | 0% |
| 20% | 1.6% |

These results show that an active ingredient that is obtained by *Cichorium intybus* root hydrolysis comprising oligofructosans does not have anti-radical activity according to the DPPH method.

B. In-Vivo Tests

I. Study of the Capacity to Reinforce the Cutaneous Barrier

The objective of this study is to quantify in vivo, on volunteers, the effects of a *Cichorium intybus* root hydrolyzate comprising oligofructosans (Example 1) formulated with 3% emulsified gel (composition of Example 8) on the negligible water loss (NWL) of the skin.

This effect was observed after 7 and 14 days of twice-daily applications and compared to a placebo after chronic artificial disruption of the barrier function using a sodium lauryl sulfate (SLS) detergent used at 10%.

Actually, the cutaneous barrier plays a regulating role in the balance of water of the skin. When the latter is damaged, misalignments in the regulation of water exchanges appear. The water then migrates more easily toward the outside medium, which increases the negligible water loss. By contrast, if the state of the cutaneous barrier improves, the values of water losses will decrease because the regulation of exchanges of water will be ensured in a correct manner.

The study was done in the winter on 20 volunteers selected according to the following criteria:

Mean age of greater than 65 years (older adults being more apt to have a vitamin D deficiency)

Feminine sex (women are a population more at risk of vitamin D deficiency)

Not taking the food supplement containing vitamin D or vitamin D supplements, and Having normal skin on the arms.

Measurements of the negligible water loss have been made using a Tewameter®, device equipped with a probe that measures the water vapor gradient being installed between the cutaneous surface and the ambient air.

The operating procedure of the study is as follows.

Between D14 and D0, the volunteers do not apply any cream on the tops of their arms.

On D0, three measuring zones are determined at the height of the arms:

Untreated zone

Placebo zone

Zone treated with the active ingredient of Example 1 that is formulated according to Example 8. Measurements of NWL are made in each zone using a Tewameter®.

Between D0 and D6:

The studied zones are washed with an irritant soap (SLS) that makes it possible to increase the water losses, The products are applied twice daily on the dedicated zones. On D7, measurements of the NWL are made on each zone with a Tewameter®.

Between D7 and D13:

The studied zones are washed with an irritant soap (SLS) that makes it possible to increase the water losses, The products are applied twice daily on the dedicated zones.

On D14, measurements of the NWL are made on each zone with a Tewameter®. The results that are obtained for the active ingredient according to the invention in percentage relative to the results that are obtained with the placebo are presented in the table below:

|  | Variation/Placebo (%) |
|---|---|
| D7 | −14.3% |
| D14 | −16.9% |

These results shows that under the conditions of this study, after 7 days of twice-daily applications and in comparison to the placebo, a *Cichorium intybus* root hydrolyzate that comprises oligofructosans according to the invention and that is formulated with 3% emulsified gel significantly reduces the negligble water loss by 14.3% after repeated damage to the SLS. This effect is also measured after 14 days of study with a significant reduction of the NWL by 16.9%.

The use of a *Cichorium intybus* root hydrolyzate comprising oligofructosans therefore makes it possible to limit the alteration of the barrier function and thus to reinforce the cutaneous barrier in mature individuals of more than 65 years of age that are apt to have a vitamin D deficiency.

II. Study of the Capacity to Accelerate the Recovery of the Barrier Function

The objective of this study is to evaluate in vivo, on volunteers, the effectiveness of a *Cichorium intybus* root hydrolyzate comprising oligofructosans, (Example 1) formulated with 3% emulsified gel (composition of Example 8), on the capacity of the barrier function to recover after a single attack using a patch containing sodium lauryl sulfate (SLS). This effect was evaluated after 7 and 14 days of twice-daily applications by measuring the negligible water loss (NWL) of the skin.

The study was done in the winter on 19 volunteers selected according to the following criteria:

Mean age of greater than 65 years (older adults being more apt to have a vitamin D deficiency)

Feminine sex (women are a population more at risk of vitamin D deficiency)

Not taking the food supplement containing vitamin D or vitamin D supplements, and Having normal skin on the arms.

The measurements of the negligible water loss have been made using a Tewameter®, a device equipped with a probe that measures the water vapor gradient being installed between the cutaneous surface and the ambient air.

The operating procedure of the study is as follows.

Between D14 and D0, the volunteers do not apply any cream on the tops of their arms.

On $D_{before\ attack}$, three measuring zones are determined on the tops of the arms:

Untreated zone

Placebo zone

Zone treated with the active ingredient of Example 1 formulated according to Example 8.

Measurements of the NWL are made in each zone using a Tewameter®. An occlusive patch of SLS is applied at 0.8% on each of the three zones. 24 hours after placement, the patches are removed.

On D0, 72 hours after the patches are removed, the measuring zones are referenced at the forearms, and measurements of the NWL are taken on each zone using a Tewameter®.

Between D0 and D14, the products (active ingredient and placebo) are applied twice daily on the dedicated zones.

On D2, D3, D4, D7, D9, D11 and D14, measurements of the NWL are made on each zone with a Tewameter®.

The results that are obtained are presented in the table below:

|  | Recovery of the Barrier Function (%) | | | | | | |
| --- | --- | --- | --- | --- | --- | --- | --- |
|  | D2 | D3 | D4 | D7 | D9 | D11 | D14 |
| Untreated Zone | 30% | 45% | 49% | 67% | 72% | 83% | 92% |
| Placebo | 30% | 44% | 50% | 68% | 75% | 82% | 91% |
| Example 8 Emulsified Gel | 36% | 51% | 58% | 72% | 80% | 88% | 94% |
| Example 8 Emulsified Gel/Placebo | 0.1809 | 0.0768 | 0.0072 | 0.0461 | 0.0324 | 0.0090 | 0.4124 |

It is noted that under the conditions of this study, after 14 days of twice-daily applications and in comparison to the placebo, a *Cichorium intybus* root hydrolyzate comprising oligofructosans formulated with 3% emulsified gel promotes a significantly faster recovery of the barrier function after a single attack and prior to the SLS. As soon as four days of application have passed, the water losses are reduced by 58%.

These results therefore show well that a *Cichorium intybus* root hydrolyzate comprising oligofructosans formulated with 3% accelerates, after an attack, the return to a normal barrier function and thus improves the recovery capacity of the skin in mature individuals that are apt to have a vitamin D deficiency.

The invention claimed is:

1. A method of treating skin with a vitamin D deficiency, comprising topically applying an effective amount of an active ingredient to a subject in need thereof, said active ingredient being designed for use in a composition with cutaneous application, comprising a *Cichorium intybus* root hydrolyzate comprising oligofructosans.

2. The method according to claim 1, wherein the effective amount of the active ingredient acts on skin cells similar to vitamin D.

3. The method according to claim 1, wherein the effective amount of the active ingredient treats the skin by stimulating signaling paths regulated by vitamin D receptors in cutaneous cells.

4. The method according to claim 1, wherein the effective amount of the active ingredient treats the skin by stimulating synthesis of vitamin D receptors and/or to increase functionality of the vitamin D receptor in cutaneous cells.

5. The method according to claim 1, wherein the effective amount of the active ingredient treats the skin by stimulating network of genes engaged in terminal differentiation of keratinocytes.

6. The method according to claim 1, wherein the effective amount of the active ingredient treats the skin by increasing expression of KLF4, cytokeratin 1, involucrin, cystatin E/M, and/or KLK5 in cutaneous cells.

7. The method according to claim 1, wherein the effective amount of the active ingredient treats the skin by promoting formation of the epidermal barrier.

8. The method according to claim 2, wherein the skin with the vitamin D deficiency is older, aged skin.

9. A method of preserving skin integrity or promoting recovery of skin barrier function, comprising topically applying to a subject in need thereof an effective amount of a composition for topical application, comprising an active ingredient designed for use in a composition with cutaneous application, comprising a *Cichorium intybus* root hydrolyzate comprising oligofructosans, the active ingredient being present between 0.01% and 3% by total weight of the composition.

* * * * *